US00PP28725P3

(12) United States Plant Patent
Velazquez

(10) Patent No.: US PP28,725 P3
(45) Date of Patent: Dec. 5, 2017

(54) ***DAPHNE* PLANT NAMED 'MONSTRK'**

(50) Latin Name: *Daphne odora*
Varietal Denomination: MonStrk

(71) Applicant: Cesar Velazquez, Salem, OR (US)

(72) Inventor: Cesar Velazquez, Salem, OR (US)

(73) Assignee: Monrovia Nursery Company, Azusa, CA (US)

( * ) Notice: Subject to any disclaimer, the term of this patent is extended or adjusted under 35 U.S.C. 154(b) by 128 days.

(21) Appl. No.: 14/756,871

(22) Filed: Oct. 21, 2015

(65) Prior Publication Data

US 2016/0120086 P1 Apr. 28, 2016

Related U.S. Application Data

(60) Provisional application No. 62/122,539, filed on Oct. 22, 2014.

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Daphne* cultivar named 'MonStrk' is disclosed, characterized by variegated leaves with a distinctive large yellow margin. Foliage is distinctively elongated. The new cultivar is a *Daphne*, suitable for ornamental garden purposes.

2 Drawing Sheets

Latin name of the genus and species: *Daphne odora*.
Variety denomination: 'MONSTRK'.

BACKGROUND OF THE INVENTION

The new cultivar is a product of a chance discovery in a commercial setting by the inventor. In 2006, the inventor, Cesar Velazquez discovered an interesting single branch mutation in a commercial planting of the unpatented parent variety *Daphne odora* 'Aureomarginata'. This single branch mutation was discovered at a commercial nursery in Dayton, Oreg.

During 2006 the inventor propagated the interesting mutation by semi-hardwood cuttings at the commercial nursery in Dayton, Oreg. The initial propagation showed the mutation to be stable and additional generations were propagated, also by semi-hardwood cuttings. Approximately 7 generations have been reproduced since 2006, and have shown that the unique features of this cultivar are stable and reproduced true to type.

SUMMARY OF THE INVENTION

The cultivar 'MonStrk' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MonStrk' These characteristics in combination distinguish 'MonStrk' as a new and distinct *Daphne* cultivar:

1. Variegated leaves with a wide yellow margin.
2. Elongated foliage.

COMPARISON TO PARENT VARIETY

Plants of the new cultivar 'MonStrk' are similar to plants of the parent; *Daphne odora* 'Aureomarginata' in most horticultural characteristics, however, plants of the new cultivar 'MonStrk' have foliage with a significantly thicker yellow margin.

COMMERCIAL COMPARISON

'MonStrk' is best compared to the commercial variety *Daphne odora* 'Rogbret' U.S. Plant Pat. No. 21,820. Plants of the new cultivar 'MonStrk' are similar to plants of 'Rogbret' in most horticultural characteristics, however, plants of the new cultivar 'MonStrk' have a broad, more open overall plant habit. Additionally, plants of 'MonStrk' produce foliage with a thicker yellow margin than foliage of 'Rogbret'.

BRIEF DESCRIPTION OF THE PHOTOGRAPHS

Figure 1:
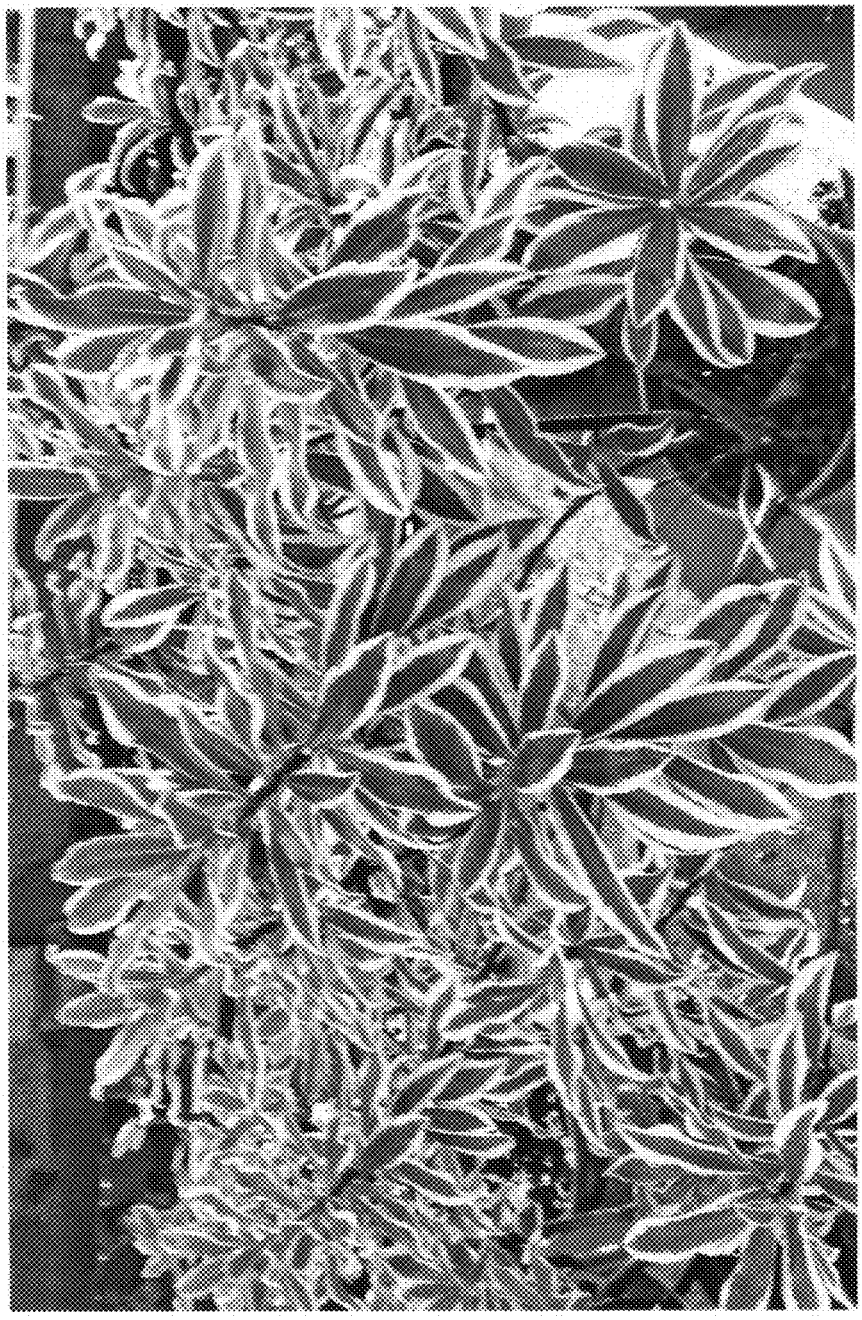

The accompanying photograph in FIG. 1 illustrates in full color a typical plant of 'MonStrk' grown outdoors in Oregon.

Figure 2:
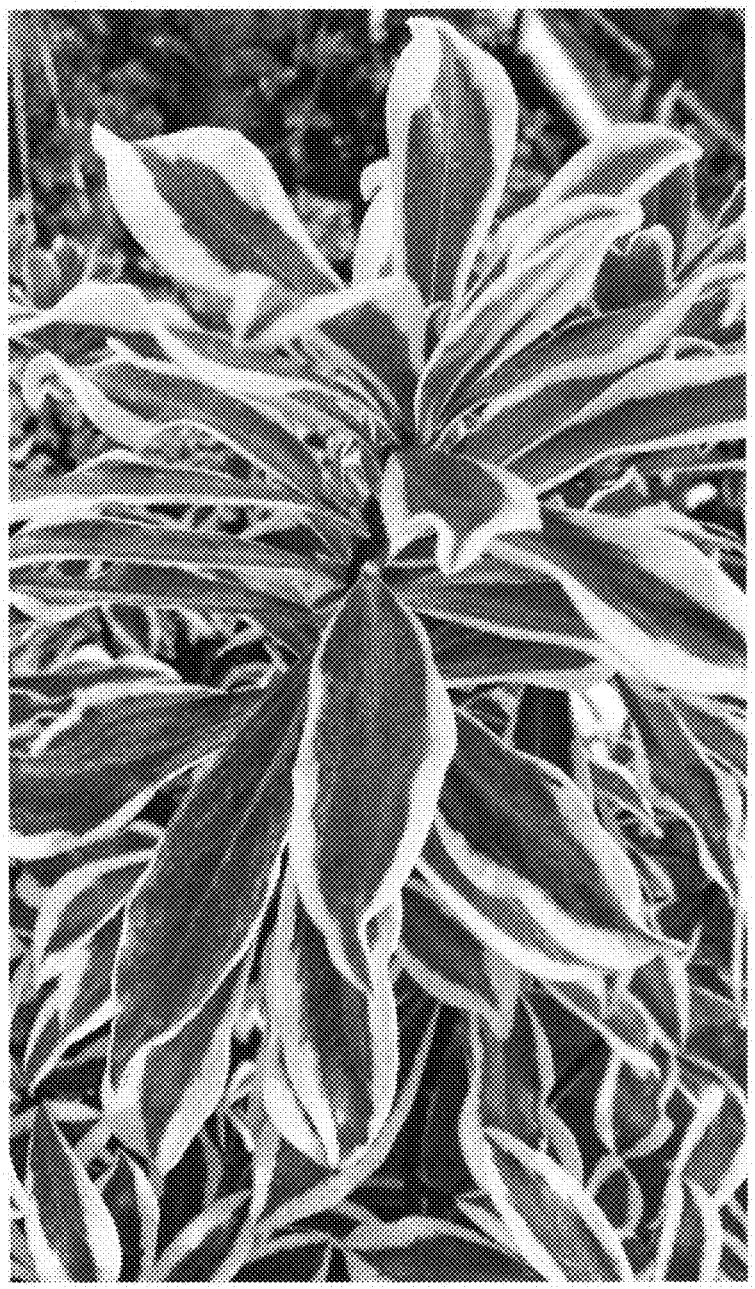

FIG. 2 illustrates in full color a close up of the foliage. The plant is approximately 2 years old, and is planted in a 1 gallon pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MonStrk' plants grown outdoors in Dayton, Oreg. Plants are approximately 2 years old, in a 1 gallon nursery container. Temperatures ranged from −8° C. to 20° C. at night to 5° C. to 35° C. during the day. Measurements and numerical values represent averages of typical plant types. Botanical classification: *Daphne odora* 'MonStrk'.

PROPAGATION

Time to rooting: Approximately 4 to 8 weeks at approximately 20° C. to 30° C. from semi-hardwood cuttings.

Root description: Fine, fibrous young roots. Older roots becoming woody.

PLANT

Growth habit: Upright and outwardly spreading evergreen shrub. Moderately dense.

Height: Approximately 50 cm.

Plant spread: Approximately 70 cm.

Branching characteristics: Above average branching for a *Daphne*, average 5 main branches, angled approximately 45 degrees on average.

Length of lateral branches: Approximately 25 cm.

Diameter of lateral branches: Approximately 0.7 cm.

Lateral branch strength: Very strong, with some flexibility.

Lateral branch color: Young branches near RHS Yellow-Green 144A. Mature branches: Near RHS Brown 200B.

Other stem or plant characteristics: No pubescence or lenticels observed. Texture moderately rough.

Number of leaves per lateral branch: Average 20 to 25.

Age of plant described: Approximately 2 years.

FOLIAGE

Leaf:

*Type*.—Simple.

*Arrangement*.—Alternate.

*Average length*.—Approximately 7.0 to 8.2 cm.

*Average width*.—Approximately 1.8 to 2.7 cm.

*Shape of blade*.—Elliptic.

*Apex*.—Mucronate or acute.

*Base*.—Attenuate.

*Attachment*.—Sessile.

*Margin*.—Entire.

*Aspect*.—Undulating.

*Texture of top surface*.—Smooth.

*Texture of bottom surface*.—Smooth.

*Leaf internode length*.—Approximately 1.0 to 1.5 cm.

*Color*.—Young foliage upper side: Center near RHS Yellow-Green 144B. Margin near Yellow 12C and 8B. Margin width ranges approximately 0.5 cm to 1.0 cm wide. Young foliage under side: Center near RHS Green 137A. Margin near 12C and 8B. Margin width ranges from approximately 0.5 cm to 2.0 cm wide. Mature foliage upper side: Center near RHS Green 137A. Margin near 12D and 8D. Margin width ranges from approximately 0.5 cm to 2.0 cm wide. Mature foliage under side: Center near RHS Green 137C. Margin near 12D and 8D. Margin width ranges from approximately 0.5 cm to 2.0 cm wide.

*Venation*.—Type: Pinnate. Venation color upper side: Near Yellow 8D. Venation color under side: Near RHS Green 138D.

Petiole: Not present, sessile.

FLOWER

Bloom period:

*Natural season*.—December to March.

Inflorescence:

*Arrangement*.—Single trumpet shaped flowers, composed of petaloid sepals clustered in terminal heads. Corolla not present.

*Diameter*.—Approximately 4.5 cm.

*Depth*.—Approximately 4.0 cm.

*Quantity of flowers per inflorescence*.—Approximately 15 to 19 open flowers and 3 to 5 buds.

Flower:

*Facing direction*.—Out and up.

*Diameter of entire flower*.—Approximately 1.5 cm.

*Depth/length of flower*.—Approximately 1.8 cm.

*Persistent or self-cleaning*.—Self-cleaning.

*Fragrance*.—Very strong, sweet *Daphne* scent.

Bud:

*Size*.—Approximately 8 mm long and 4 mm wide.

*Shape*.—Conical.

*Color*.—Near RHS Red-Purple 69C, upper section lightly flushed near RHS Red-Purple 70B.

Petaloid sepals:

*Quantity*.—4.

*Length*.—Approximately 0.9 cm, excluding tube.

*Width*.—Approximately 0.4 cm.

*Apex*.—Acute.

*Base*.—Fused

*Shape*.—Deltoid.

*Margin*.—Entire, slightly rolled inward.

*Arrangement*.—Each petal opposite another, forming a cross.

*Texture*.—Smooth upper and lower surfaces.

*Color*.—Upper surface at first opening: Near RHS Red-Purple 69B, heavily flushed near RHS Red-Purple 70B. Upper surface at maturity: Near RHS Red-Purple 69C with occasional slight margin flushed near RHS Red-Purple 70C. Upper surface at fading: Near RHS White N155B. Under surface at first opening: Near RHS Red-Purple 69B, heavily flushed near RHS Red-Purple 70B. Under surface at maturity: Near RHS Red-Purple 73D. Under surface at fading: Near RHS Red-Purple 65D.

Floral tube:

*Length*.—Approximately 0.7 cm.

*Diameter*.—Approximately 0.4 cm.

*Color*.—Outer surface at first opening: Near RHS Red-Purple 70C. Outer surface at maturity: Near RHS Red-Purple 69C. Outer surface at fading: Near RHS Red-Purple 69D Inner surface at first opening: Near RHS Red-Purple 69B, occasional small blotch near 70A. Inner surface at maturity: Near RHS Red-Purple 65D. Inner surface at fading: Near RHS Red-Purple 69D.

Pedicle:

*Length*.—Average range 8 mm to 1.5 cm.

*Color*.—Near RHS Yellow-Green 144A.

REPRODUCTIVE ORGANS

Number of pistils per flower: 1.

*Pistil length*.—Approximately 0.6 cm.

*Stigma shape*.—Linear.

*Stigma color*.—Near RHS White N155B.

*Style color*.—Near RHS White N155B.
*Style length*.—Approximately 0.5 cm.
*Ovary color*.—Near RHS Yellow-Green 144C.
*Stamens quantity*.—Approximately 5 to 10. Stamens semi-fused to sepals.
*Stamen length*.—Approximately 0.2 cm.
*Stamen width*.—Less than 1 m.
*Stamen color*.—Near RHS White N155B.
*Anther shape*.—Linear

OTHER CHARACTERISTICS

Disease and pest resistance: Not observed to be susceptible nor resistant to normal diseases and pests of *Daphne odora*.

Drought tolerance: Some drought tolerance. Plants will not wilt or suffer significant damage if regular supplemental waterings are missed.

Low temperature tolerance: Hardy in to −20° C.

High temperature tolerance: High temperature tolerance is not exactly known. Tolerates at least 33° C.

Fruit/seed production: Not observed to date. Floral parts dry up, fruits nor formed.

What is claimed is:

1. A new and distinct cultivar of *Daphne* plant named 'MonStrk' as herein illustrated and described.

* * * * *